US008323951B2

(12) United States Patent
Garault et al.

(10) Patent No.: US 8,323,951 B2
(45) Date of Patent: Dec. 4, 2012

(54) STRAINS OF *LACTOBACILLUS HELVETICUS* WHICH DO NOT FERMENT LACTOSE

(75) Inventors: Peggy Garault, Monthery (FR); Anne Druesne, Villiers le Bacle (FR); Jean-Michael Faurie, Jouy en Josas (FR); Claire Queguiner, Fontenay aux Roses (FR); Thierry Saint-Dennis, Vincennes (FR); Tamara Smokvina, Orsay (FR)

(73) Assignee: Compagnie Gervais Danone, Paris (FR)

( * ) Notice: Subject to any disclaimer, the term of this patent is extended or adjusted under 35 U.S.C. 154(b) by 992 days.

(21) Appl. No.: 12/279,951

(22) PCT Filed: Feb. 19, 2007

(86) PCT No.: PCT/FR2007/000294
§ 371 (c)(1),
(2), (4) Date: Aug. 19, 2008

(87) PCT Pub. No.: WO2007/096510
PCT Pub. Date: Aug. 30, 2007

(65) Prior Publication Data
US 2009/0088391 A1    Apr. 2, 2009

Related U.S. Application Data

(60) Provisional application No. 60/774,654, filed on Feb. 21, 2006.

(30) Foreign Application Priority Data

Feb. 20, 2006   (EP) .................................... 06290286

(51) Int. Cl.
C12N 1/20 (2006.01)
A01N 63/00 (2006.01)
A23C 9/12 (2006.01)

(52) U.S. Cl. ..................... 435/252.9; 424/93.45; 426/61
(58) Field of Classification Search ........................ None
See application file for complete search history.

(56) References Cited

U.S. PATENT DOCUMENTS

| 4,452,859 A | 6/1984 | Nishijima et al. |
| 4,599,313 A | 7/1986 | Gonzalez |
| 6,331,140 B1 * | 12/2001 | Mollet et al. ................. 435/476 |
| 6,534,304 B1 * | 3/2003 | Yamamoto et al. ......... 435/252.9 |
| 6,972,282 B1 * | 12/2005 | Tossavainen et al. ........ 514/15.7 |

FOREIGN PATENT DOCUMENTS

| EP | 0583074 | 2/1994 |
| EP | 0652285 | 5/1995 |
| EP | 0965643 | 12/1999 |
| EP | 1016709 | 7/2000 |
| WO | WO-00/15042 | 3/2000 |
| WO | WO-01/88150 | 11/2001 |

OTHER PUBLICATIONS

Callanan et al., Genetic diversity in the lactose operons of *Lactobacillus helveticus* strains and its relationship to the role of these strains as commercial starter cultures, *Appl. Environ. Microbiol.* 71: 1655-8 (2005).
Fortina et al., Mapping of three plasmids from *Lactobacillus helveticus* ATCC 15009, *Lett. Appl. Microbiol.* 17: 303-6 (1993).
Hata et al., A placebo-controlled study of the effect of sour milk on blood pressure in hypertensive subjects, *Am. J. Clin. Nutr.* 64: 767-71 (1996).
Jauhiainen et al., *Lactobacillus helveticus* fermented milk lowers blood pressure in hypertensive subjects in 24-h ambulatory blood pressure measurement, *Am. J. Hypertension.* 18: 1600-5 (2005).
Masuda et al., Antihypertensive peptides are present in aorta after oral administration of sour milk containing these peptides to spontaneously hypertensive rats, *J. Nutr.* 126: 3063-8 (1996).
Prestini et al., Correlation between plasmid DNA, lactose fermentation and proteolytic activity in *Lactobacillus helveticus* and *Lactobacillus bugaricus, Annali Della Facolta Di Agraria, Universita Cattolica Del Sacro Cuore*, 23: 71-84 (1983). (English translation of summary).
Soda et al., Adjunct Cultures: Recent Development and Potential Significance to the Cheese Industry, *Journal of Dairy Science, American Dairy Science Association*, Savory, IL, US, 83: 609-19 (2000).
Yamamoto et al., Antihypertensive effects of different kinds of fermented milk in spontaneously hypertensive rats. *Biosci. Biotechnol. Biochem.* 58: 776-8 (1994).
Zwahlen et al., ISL2, a new mobile genetic element in *Lactobacillus helveticus, Mol. Gen. Genet.* 245: 334-8 (1998).

* cited by examiner

*Primary Examiner* — Irene Marx
(74) *Attorney, Agent, or Firm* — Marshall, Gerstein & Borun LLP

(57) ABSTRACT

The invention relates to novel strains of *Lactobacillus helveticus*. More specifically, the invention relates to strains of *Lactobacillus helveticus* having a lactose-negative phenotype and to the uses thereof in the agri-food industry. The invention also relates to a method for obtaining such strains of *Lactobacillus helveticus*.

Figure 1:
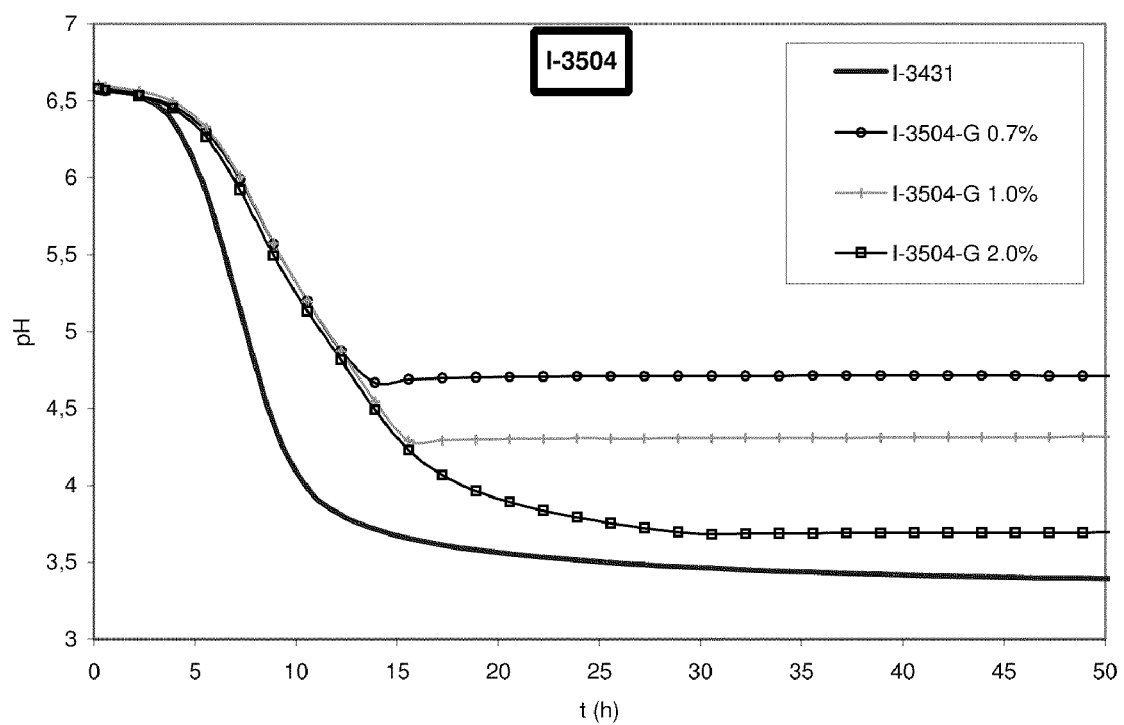

23 Claims, 5 Drawing Sheets y-axis: IC50 (microliters of fermented milk supernatant per milliliter of reaction medium)

x-axis: lait = milk

STRAINS OF *LACTOBACILLUS HELVETICUS* WHICH DO NOT FERMENT LACTOSE

This application is a U.S. National Phase of International Patent Application No. PCT/FR2007/00294, filed Feb. 19, 2007, which claims the benefit of priority of U.S. Provisional Application No. 60/774,654, filed Feb. 21, 2006 and European Patent Application No. 06290286.1, filed Feb. 20, 2001. The disclosure of each priority document is incorporated hereby reference in its entirety.

The present invention relates to novel strains of *Lactobacillus helveticus*, as well as their uses in the agri-food field. More particularly, the present invention proposes strains of *Lactobacillus helveticus* possessing a lactose-negative phenotype. The present invention also relates to a process for obtaining such strains of *Lactobacillus helveticus*.

Hypertension affects a significant proportion of the population. The use of the peptide VPP (Val Pro Pro) and peptides containing the sequence VPP as agents capable of reducing blood pressure by inhibition of the angiotensin converting enzyme (ACE) has been described in EP 0 583 074. A similar effect of the tripeptide IPP (Ile Pro Pro) has also been described in the literature. These peptides inhibit the ACE by blocking its active site and thus preventing it from activating the angiotensin.

It is known that the two sequences VPP and IPP are present in bovine Beta casein and that suitable hydrolysis of this casein (or more generally of the milk which contains it) makes it possible to obtain said tripeptides. Numerous animal and human studies have shown that the daily ingestion of a few milligrams of these tripeptides makes it possible to effectively reduce blood pressure, in particular in hypertensive subjects, reducing all the more the risk of cardio-vascular accident.

Peptides originating from a milk fermented by *Lactobacillus helveticus* have shown their ACE inhibiting (ACEI) effect in vivo and these peptides have been found in the aortas of rats having participated in the study (Masuda O. et al., 1996. J. Nutr. 126, 3063-8). Other studies have also shown more specifically a reduction in blood pressure in hypertensive rats following the ingestion of peptides originating from a milk fermented by *L. helveticus* (Yamamoto N. et al., 1994. Biosci. Biotech. Biochem. 58, 776-8).

In humans, the same fermented milk has also made it possible to reduce systolic arterial pressure (Hata et al.; 1996. Am. J. Clin. Nutr., 64, 767-71). A more recent study confirms that the peptides present in the product AMEAL S® marketed by the company CALPIS significantly reduce blood pressure in subjects having higher than normal blood pressure (Mizuno et al., 2005. British Journal of Nutrition; vol 94, issue 1, 84-91).

Another recent study (Jauhiainen et al.; 2005. Am. J. of Hypertension, 18: 1600-1605) puts forward the hypothesis that the abovementioned action mechanism (ACE inhibition) for explaining the antihypertensive effect of a milk fermented by an *L. helveticus* could not however be the determining action mechanism in humans.

A large majority of *Lactobacillus helveticus* is capable of producing the tripeptides IPP and VPP by fermentation of milk, but the quantities produced can be variable. EP 1 016 709 describes a means of producing the tripeptides VPP and IPP by fermentation of milk using specific strains of lactic bacteria belonging to the species *Lactobacillus helveticus*. However, the product thus manufactured (fermented milk) contains a very large quantity of lactic acid, and is therefore characterized by an acidity which is unacceptable from the sensory and gustatory point of view. Moreover, the problem of post-acidification arises: even if fermentation is stopped (in a standard fashion by cooling down) at organoleptically acceptable pHs (pH>4), the acidification continues at a low temperature due to the intrinsic properties of *Lactobacillus helveticus*. This leads to a drop in the pH of the product, which also becomes quite unacceptable for consumption.

In order to avoid post-acidification, it is possible to stop the fermentation at an acceptable pH by immediately killing the strain by heat treatment (pasteurization, thermization): post-acidification is then zero (the acidity of the product no longer develops during its storage). Unfortunately, the quantity of tripeptides is reduced due to the early stopping of the fermentation. The products thus obtained then have only low IPP and VPP contents. It is also possible to ferment the milk with the same strain until a maximum tripeptide concentration is obtained. The large quantity of lactic acid generated in parallel must then be removed by a complex and expensive multi-stage process. Moreover, the process is not "natural", as it involves separation stages. Such a process is thus not suited to an industrial scale.

The present invention proposes solutions to the drawbacks of the state of the art. In particular, the present invention proposes strains of *Lactobacillus helveticus* allowing the preparation of food products, in particular fermented dairy products, possessing numerous advantageous properties:

The dairy products according to the invention have a perfectly controlled acidity, not only at the end of fermentation, but also during storage. In particular, they are not subject to the post-acidification phenomenon. Thus, the dairy products according to the invention are organoleptically very satisfactory.

The dairy products according to the invention can be consumed directly as probiotics, i.e. they contain a significant quantity of live bacteria, without any impact on their gustatory qualities and, in particular, without any impact on their acidity.

The preparation of the products according to the invention requires no thermization stage, nor any complex purification stage. The processes according to the invention can thus be implemented simply, in standard dairy installations, without significant modification of the equipment. Moreover, the processes according to the invention are completely natural.

Food products, in particular dairy products, according to the invention can contain very high levels of tripeptides VPP and IPP, with high (IPP+VPP)/(lactic acid) ratios. These results can be obtained without a prior purification or concentration stage.

Food products, in particular dairy products, according to the invention advantageously contain a significant biomass (i.e a significant concentration of living micro-organisms).

By strain is meant, within the meaning of the present invention, any culture, generally pure, of a micro-organism obtained from a single cell or an isolated colony.

By variant or mutant of a strain X is meant, within the meaning of the present invention, any strain obtained from a reference strain X. In the present context, the term "variant" is used more particularly to designate a strain obtained chiefly by mutation and selection from a reference strain X and the term "mutant" to designate more specifically a strain obtained by random or directed mutagenesis techniques (for example genetic transformation using vectors), applied to strain X.

The mutants or variants of the strains according to the present invention are of course covered by the protection conferred by this patent once they retain the essential aspects of the invention, in particular the lactose-negative phenotype.

By "lactose-negative phenotype" strain is meant any strain not having the ability to convert lactose into lactic acid.

By "fructose-negative phenotype" strain is meant any strain not having the ability to metabolize fructose.

By dairy medium is meant any medium containing milk proteins, for example a bovine milk standardized at 4% proteins with bovine milk powder (skimmed or not skimmed) or with concentrated milk.

By dairy product, within the meaning of the present invention, is meant, in addition to milk, any product derived from milk, such as cream, ice cream, butter, cheese, yogurt, fermented milk; by-products, such as lactoserum and casein as well as various prepared foods containing milk or milk constituents as main ingredient. Among dairy products, fermented dairy products include among other things yogurts, fermented milks, cottage cheeses, kefirs, cheeses, probiotic dairy products and more generally any dairy product which has undergone at least one fermentation stage. Said milk is generally cow's milk, but can also be milk from other mammals, such as goat, ewe, mare, camel or buffalo.

By food product, within the meaning of the present invention, is meant any product intended for human or animal nutrition. In particular, the food products include products intended for feeding infants, children, adolescents and adults. All or part of the food products according to the invention can contain at least one fermented dairy product according to the invention. The food products according to the invention can also contain other ingredients usually used in the agri-food industry, such as additives, preservatives, fruits or fruit extracts, flavourings, colourings, texturizing agents, cereals, pieces of chocolate, etc.

By ferment is meant, within the meaning of the present invention, any composition containing at least one living micro-organism strain capable of fermenting a given medium. Among the ferments, the lactic ferments are compositions containing at least one living micro-organism strain capable of fermenting a dairy medium.

According to an embodiment, the present invention relates to a strain of *Lactobacillus helveticus* not having the ability to convert lactose into lactic acid. The present invention also relates to a strain of *Lactobacillus helveticus* not having the ability to convert lactose into lactic acid, and possessing at least one mutation in the lactose operon.

According to an embodiment, said mutation in the lactose operon is a point mutation introducing a stop codon. According to a still more preferred embodiment, said point mutation introducing a stop codon is situated in the lacL gene of the lactose operon. By point mutation is meant any nucleotide substitution involved in the sequence, by comparison with a so-called "wild-type" sequence. A person skilled in the art knows how to identify a stop codon (also called a nonsense codon), which corresponds generally in mRNA terms to one of the triplets: UAA, UAG, UGA.

Thus, the strains *Lactobacillus helveticus* according to the invention do not have the ability to degrade lactose (no conversion of lactose into lactic acid). In fact, the strains according to the invention have a lactose-negative phenotype. On the other hand, they are capable of growing in the presence of glucose as a source of carbon (fermentation of the glucose into lactic acid), and of metabolizing certain components of the milk, in particular the proteins.

Thus, the strains according to the invention advantageously allow fermentation at a completely controlled pH: the final pH after fermentation is perfectly controlled according to the quantity of glucose initially contained in the fermentation medium. This results from the fact that a given quantity of glucose results, in a virtually stoichiometric manner, in the same quantity of lactic acid. Moreover, the use of the strains according to the invention avoids any post-acidification phenomenon. Thus, thanks to the strains according to the invention, it is possible to obtain food products which are particularly satisfactory organoleptically.

Advantageously, according to an embodiment, the strains of *Lactobacillus helveticus* according to the invention are such that a dairy medium with 4.0% total proteins containing 1.0% (w/w) of glucose fermented by said strains of *Lactobacillus helveticus* for a maximum fermentation time of 30 hours, at a temperature between 30 and 45° C., have a pH greater than or equal to 4.0; preferably greater than or equal to 4.1; preferably greater than or equal to 4.2; preferably greater than or equal to 4.3; preferably greater than or equal to 4.5.

This advantage is therefore particularly marked in the case of strains of *Lactobacillus helveticus* which are hyperproducers of tripeptides IPP and/or VPP: it is absolutely not required to compromise between a high level of production of tripeptides during the fermentation (requiring as long a fermentation time as possible), and organoleptically acceptable properties (requiring limited acidification, and therefore, not only as short a fermentation time as possible, in order to limit the production of lactic acid by fermentation, but also thermization/pasteurization in order to avoid the post-acidification phenomenon).

In fact, advantageously according to the present invention, the production of tripeptides VPP and/or IPP, and the production of lactic acid are partially decoupled: the production of lactic acid is only a function of the quantity of glucose initially present in the fermentation medium, and no longer a function of the fermentation time.

A means of expressing the concentration of tripeptides simply is to express it as a concentration of VPP equivalent [VPPeq].

This is expressed in mg/kg: [VPPeq]=[VPP]+(9/5× [IPP])

Thus, according to an embodiment, the strains of *Lactobacillus helveticus* according to the invention are advantageously capable, by fermentation, of producing the tripeptides of sequence IPP and/or VPP in a quantity of at least 25 mg, preferably at least 30 mg, preferably at least 35 mg, preferably at least 40 mg, preferably at least 45 mg, preferably at least 50 mg, preferably at least 55 mg, preferably at least 60 mg, preferably at least 65 mg, preferably at least 70 mg, preferably at least 75 mg, more preferably at least 80 mg of VPPeq per kg of fermented product. Such quantities of VPP and/or IPP are generally obtained by fermentation with a strain according to the invention at a temperature between 30 and 45° C., preferably between 31 and 44° C., preferably between 32 and 43° C., preferably between 33 and 42° C., preferably between 34 and 41° C., preferably between 35 and 40° C., and more preferably at 37° C., of a dairy medium containing a quantity of glucose greater than 3% (w/w) and with a total proteins content greater than or equal to 2% (w/w), preferably between 2 and 10% (w/w), more preferably between 2.5 and 6% (w/w) and still more preferably equal to 4% (w/w), According to an embodiment, the strains of *Lactobacillus helveticus* according to the invention also possess a fructose-negative phenotype. The combination of the lactose-negative and fructose-negative phenotypes is particularly advantageous. In fact, fructose has a strong sweetening power, and is a useful ingredient in food products. Thus, if the fructose cannot be degraded by the strain of *Lactobacillus helveticus*, the food product retains excellent organoleptic properties. Moreover, a strain which is both lactose-negative and fructose-negative can grow only in a medium containing glucose. Thus, the final pH is advantageously better controlled in the case where the food product contains a preparation of fruit(s), in particular fruit pieces and/or juice.

According to an embodiment, the strain according to the invention is chosen from:
- I-3504 deposited at the CNCM on 14 Oct. 2005;
- I-3505 deposited at the CNCM on 14 Oct. 2005;
- I-3508 deposited at the CNCM on 14 Oct. 2005;
- and the variant or mutant strains derived from these strains.

The CNCM is the Collection Nationale de Culture de Microorganismes and has an address of 25 street Dr Roux 75724 Paris Cedex 15.

According to another embodiment, the present invention relates to the use of a strain of *Lactobacillus helveticus* according to the invention, for the preparation of a food or pharmaceutical product, in particular a fermented dairy product.

Advantageously, according to an aspect of the invention, said food or pharmaceutical product possesses anti-hypertensive properties.

The present invention also relates to a food product, in particular a fermented dairy product, comprising at least one strain of *Lactobacillus helveticus* according to the invention.

Advantageously, according to an embodiment, said food product contains at least $10^6$, preferably at least $10^7$, preferably at least $10^8$ CFU/mL of live *Lactobacillus helveticus* bacteria. Thus, the food product according to the invention contains a significant biomass.

According to an embodiment, said food product contains at least 25 mg, preferably at least 30 mg, preferably at least 35 mg, preferably at least 40 mg, preferably at least 45 mg, preferably at least 50 mg, preferably at least 55 mg, preferably at least 60 mg, preferably at least 65 mg, preferably at least 70 mg, preferably at least 75 mg, more preferably at least 80 mg of VPPeq. per kg of food product.

According to an embodiment, the food product according to the invention also comprises preparations of fruit(s), in particular fruit pieces and/or juice.

According to an embodiment, the food product according to the invention possesses a pH greater than or equal to 3.85; preferably greater than or equal to 3.90; preferably greater than or equal to 3.95; preferably greater than or equal to 4.00; preferably greater than or equal to 4.05; preferably greater than or equal to 4.10; preferably greater than or equal to 4.15; more preferably greater than or equal to 4.20.

Advantageously according to an embodiment, the food product according to the invention possesses anti-hypertensive properties.

According to another aspect, the present invention relates to a process for the preparation of a food product.

According to an embodiment, said process comprises the following stages:
- selecting a raw material containing milk proteins, in particular proteins containing the peptide sequences IPP and/or VPP. This can for example be milk containing 2-10% (w/w) total proteins.
- selecting at least one *Lactobacillus helveticus* strain according to the invention,
- seeding said raw material with said strain, fermenting said raw material in the presence of 1-3% (w/w) glucose for 12-30 hours at 30-45° C., and in the presence of said strain.

According to an embodiment, the process according to the invention advantageously has no thermization stage after fermentation. This makes it possible to retain live bacteria in the (probiotic) food product.

According to an embodiment, the present invention relates to a use of streptozotocin for obtaining *Lactobacillus helveticus* strains possessing a lactose-negative phenotype.

The present invention also provides a process for obtaining such strains of *Lactobacillus helveticus*.

According to an embodiment, said process for obtaining *Lactobacillus helveticus* strains possessing a lactose-negative phenotype, comprising the following stages:
- providing at least one strain of *Lactobacillus helveticus*;
- bringing said at least one strain in contact with an effective quantity of streptozotocin in the presence of lactose;
- isolating the colony or colonies of lactose-negative phenotype.

The population of cells of *Lactobacillus helveticus* capable of surviving in the presence of streptozotocin is indeed advantageously extremely enriched with lactose-negative cells.

According to an embodiment, a stage involving a colorimetric test on a medium containing Xgal and/or Sgal and/or any other compound which is linked by a β-galactoside bond to galactose and which can be tagged following the breaking of this bond by the microorganism, is added to said process for obtaining strains according to the invention. IPTG can be also added in order to carry out this test since this compound acts as an inducer of the lactose transporter or as an inducer of the use of lactose by the microorganism.

By way of example, said process can be carried out as follows:
- 1st subculture of the starting *Lactobacillus helveticus* strains (mother strains), on neutral MRS (Man Rogosa Sharp) broth, overnight at 35-40° C.;
- 2nd subculture in neutral MRS.
- Incubation until a sufficient biomass is obtained, for example 10-30 hours at 35-40° C.
- Seeding of MRS containing a concentration of lactose making it possible to obtain a sufficient biomass, for example 2-7% (w/w); incubation with monitoring of the OD at 580 nm.
- The streptozotocin is prepared extemporaneously, and is added during fermentation, in order to have a final concentration which is bactericidal for the strain considered. This concentration is strain-dependent.
- After incubation at 35-40° C., the cultures are washed twice with tryptone salt.
- The pellets are taken up in tryptone salt, then neutral MRS broths are re-cultured
- Incubation at 35-40° C., until there is growth of the strain.
- Isolations are then carried out on neutral MRS+Xgal+ IPTG, followed by incubation at 35-40° C. under CO2. This stage is a colorimetric test making it possible to determine whether a bacterial strain is lactose-positive or lactose-negative: If the strain is capable of using the lactose as a source of carbon, there is production of a blue substance, the colony is therefore blue and in the opposite case (lactose-negative strain), it is white.
- The white colonies are subcultured on neutral MRS and incubated at 35-40° C.

The invention is further described using the following examples, which are non-limitative.

EMBODIMENT EXAMPLES

Example 1

Obtaining Strains Possessing a Lactose-negative Phenotype

Material and Methods
Starting Strains (So-called "Mother Strains")
I-3431 deposited at the CNCM on 25 May 2005

I-3434 deposited at the CNCM on 25 May 2005
I-3435 deposited at the CNCM on 25 May 2005

Test for Sensitivity to Streptozotocin

In a first phase, it is verified that the mother strains are sensitive to the antibiotic used, streptozotocin. The optical density (OD) at 580 nm is monitored on cultures at 42° C. in neutral MRS (Man Rogosa Sharp) broth. When the latter reaches 0.1, streptozotocin is added to a tube in order to finally have 50 µg/ml (for example 100 µl of a 5 mg/ml solution for 10 ml of medium).

Selection of Lactose-negative Strains

The following stages are carried out in order to obtain lactose-negative *Lactobacillus helveticus* strains:

1st subculture of the starting *Lactobacillus helveticus* strains (mother strains) from wells of the working stock, on neutral MRS medium, overnight at 37° C.;
  2nd subculture at 1% in neutral MRS.
  Incubation for 16 hours at 37° C.
  Seeding of 10 ml of MRS at 5% (w/w) lactose, at 1% and incubation at 40° C. with monitoring of the OD at 580 nm.
  The streptozotocin is prepared extemporaneously, and is added after fermentation for 2 hours 15 minutes or 4 hours, in order to have a final concentration of 50 µg/ml.
  After incubation for 7 hours 30 minutes at 40° C., the cultures are washed twice with tryptone salt.
  The pellets are taken up in 2 ml of tryptone salt, then neutral MRS media are seeded at 10%.
  Incubation at 37° C., until there is growth of the strain.
  Isolations are then carried out on neutral MRS+Xgal+ IPTG, followed by incubation at 37° C. under $CO_2$. This stage is a colorimetric test making it possible to determine whether a bacterial strain is lactose-positive or lactose-negative: If the strain is capable of using the lactose as a source of carbon, there is production of a blue substance, the colony is therefore blue and in the opposite case (lactose-negative strain), it is white.
  The white colonies are subcultured on neutral MRS and incubated at 37° C.

Results

This made it possible to obtain the following strains, possessing a lactose-negative phenotype which were then the subject of deposits at the CNCM (Collection Nationale de Cultures de Micro-organismes), 28 rue du Docteur Roux, 75724 Paris, France, in accordance with the provisions of the Budapest Treaty:

I-3504 deposited at the CNCM on 14 Oct. 2005; originating from the mother strain I-3431
  I-3505 deposited at the CNCM on 14 Oct. 2005; originating from the mother strain I-3434
  I-3508 deposited at the CNCM on 14 Oct. 2005; originating from the mother strain I-3435

The lactose-negative phenotype of the strains obtained is again confirmed on a MRS+Xgal+IPTG neutral gelose medium (so-called "white/blue" staining test)

Example 2

Strains Possessing a Lactose-negative Phenotype

The strain I-3504, deposited on 14 Oct. 2005 at the CNCM (Collection Nationale de Cultures de Micro-organismes), 28 rue du Docteur Roux, 75724 Paris, France, in accordance with the provisions of the Budapest Treaty, is a strain of *Lactobacillus helveticus* possessing the following properties:
  Lactose-negative; Fructose-negative
  production of IPP and VPP: see FIGS. 4 and 5
  acidification properties: see FIG. 1
  ACE inhibition: see FIG. 6

The strain I-3505 deposited on 14 Oct. 2005 at the CNCM (Collection Nationale de Cultures de Micro-organismes), 28 rue du Docteur Roux, 75724 Paris, France, in accordance with the provisions of the Budapest Treaty, is a strain of *Lactobacillus helveticus* possessing the following properties:
  Lactose-negative; Fructose-negative
  production of IPP and VPP: see FIG. 5
  acidification properties: see FIG. 2

The strain I-3508, deposited on 14 Oct. 2005 at the CNCM (Collection Nationale de Cultures de Micro-organismes), 28 rue du Docteur Roux, 75724 Paris, France, in accordance with the provisions of the Budapest Treaty, is a strain of *Lactobacillus helveticus* possessing the following properties:
  Lactose-negative; Fructose-negative
  production of IPP and VPP: see FIG. 5
  acidification properties: see FIG. 3

1. Measurement of the Acidification Properties of the Different Variant Strains

The acidification properties are evaluated as follows:

A medium containing 120 g of skimmed milk powder (SMP) in 930 ml of water is pasteurized for 10 minutes at 95° C. This medium is seeded at 0.5%, then subjected to fermentation at 37° C. in the presence of different concentrations of glucose. (The abbreviation Gx indicates a concentration of x % (w/w) of glucose in the medium before fermentation). The pH is then monitored as a function of time, for different strains. A sample of fermented medium taken at 30 hours of fermentation is used for measurements of production of the tripeptides IPP and VPP as well as for measurements of ACEI activity the results of which are given below.

Figure 2:
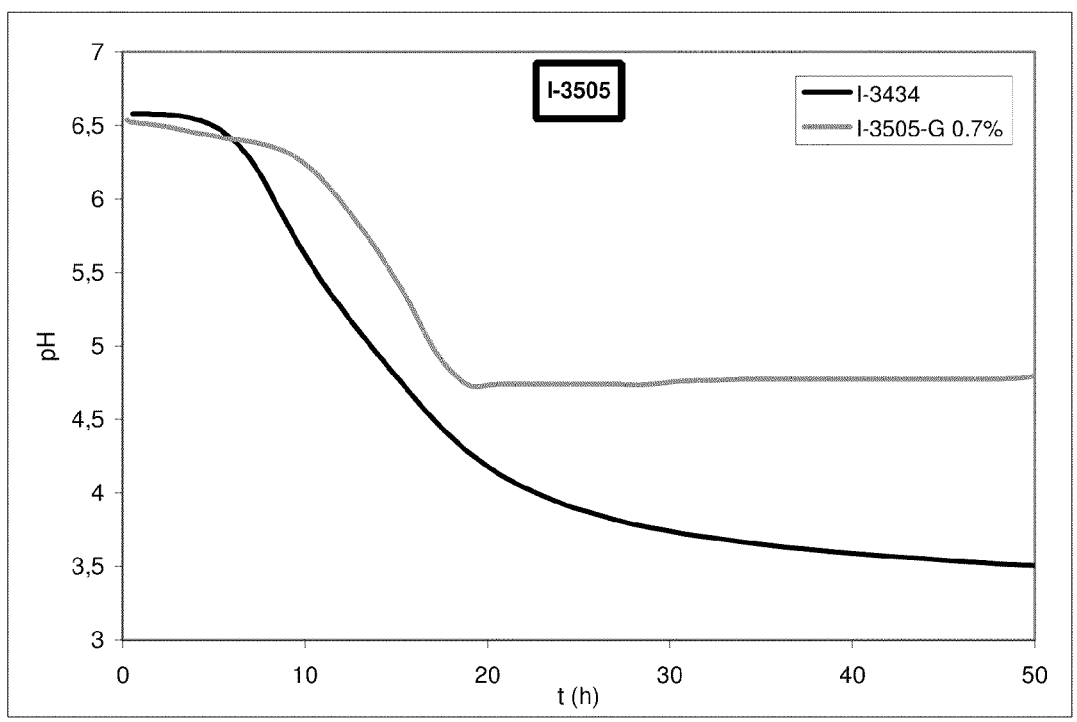
Figure 3:
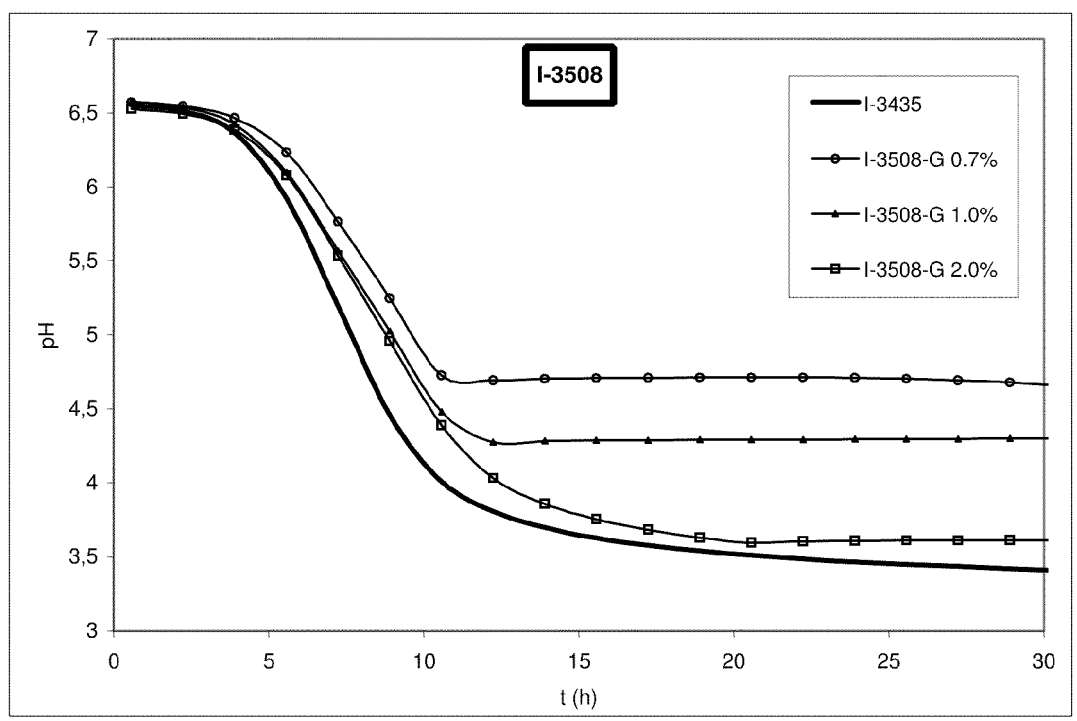

For I-3504, the results of the mother strain are also shown (I-3431, lactose-positive strain), (see FIG. 1)
For I-3505, the results of the mother strain are also shown (I-3434, lactose-positive strain), (see FIG. 2)
For I-3508, the results of the mother strain are also shown (I-3435, lactose-positive strain), (see FIG. 3)

The results shown in FIGS. 1-3 show that the strains according to the invention advantageously make it possible to finely control the pH at the end of fermentation according to the quantity of glucose initially present in the medium. Moreover, the fermentation by lactose-negative strains advantageously leads to high pH values, which will give organoleptically acceptable food products.

2. Measurement of the Production of the Tripeptides IPP and VPP

Material and Method

A sample of dairy medium taken at 30 hours of fermentation, as described previously under point 1 is used in order to carry out this measurement.

The analysis of the peptides content, in particular the content of tripeptides IPP and VPP, is carried out with an HPLC liquid chromatography method coupled to an MS/MS type detector as described hereafter:

Due to the interferences inherent in the analysis of complex samples, the use of deuterated internal standards added in a known quantity and controlled at the time of the preparation of the sample is strongly advised.

The preparation of the sample is carried out by dilution of the fermented medium in a mixture of water, methanol and trifluoroacetic acid (50/50/0.1%), containing 25 ppm of deuterated VPP internal standard (denoted hereafter VPPd, of formula H-Val [D8]-Pro-Pro-OH, MM=319.45 g/mol, available from the company Bachem Chemicals, France) and 10 ppm of deuterated IPP internal standard (denoted hereafter IPPd, of formula H-Ile [D10 N15]-Pro-Pro-OH, MM=336.2 g/mol, available from the company NEOMPS, Group SNPE, 7 rue de Boulogne, 67100 Strasbourg, France) in a ratio of 1 to 3 (for example, precise weighing in an Eppendorf of 600 mg of sample in 1200 mg of water-methanol-TFA mixture containing the internal standards).

This diluted sample is then centrifuged at 14000 g for 15 minutes. The clear supernatant obtained, containing the peptides produced during the fermentation, is then diluted precisely to 1/50th in a mixture of water-methanol (50/50, v/v) containing 0.1% trifluoroacetic acid.

The diluted solution thus obtained is then analyzed in an HPLC chromatographic system of Agilent 1100 type (company Agilent Technologies France, 1 rue Galvani 91745 Massy Cédex, France), equipped with a column suitable for the analysis of the peptides, of Waters Biosuite® type (3 mm 2.1×150 mm, C18 PA-A, WAT186002427, Waters France, 5, Rue Jacques Monod, 78280 Guyancourt) at a temperature of 50° C., flow rate of 0.25 ml/min. The peptides are eluted in standard manner with a increasing gradient of solvent B (Acetonitrile+0.100% of formic acid) in solvent A (Water+ 0.106% formic acid), over a period of 35 minutes to 2 hours depending on the desired chromatographic resolution. The method suitable for the assay of the peptides IPP and VPP uses the following gradient:

| Time | % Buffer A | % Buffer B |
|---|---|---|
| 0 | 100 | 0 |
| 3 | 96 | 4 |
| 6 | 89 | 11 |
| 15 | 60 | 40 |
| 18 | 0 | 100 |
| 21 | 100 | 0 |
| 24 | 0 | 100 |
| 27.5 | 100 | 0 |
| 35 | 100 | 0 |

The detection is carried out using a specific MS/MS type detector, for example with a device with an ion trap such as the Esquire 3000+(Bruker Daltonique, rue de l'Industrie, 67166 Wissembourg Cédex), electrospray ionization parameter in positive mode, either for the overall analysis of the peptide content (MS-MS mode), or for the precise and specific quantification of a peptide from its characteristic fragments (MRM mode). In the case of the assay of the peptides IPP and VPP, but also of the internal standards IPPd and VPPd, these peptides are isolated from their specific mass (monocharged ions 312.2 Da for VPP; 326.2 Da for IPP; 320.2 Da for VPPd; 337.3 Da for IPPd) and quantified from the intensity of their specific ions after fragmentation (fragments>=85 Da).

The integration of the chromatographic peaks of each of the peptides IPP, VPP and the comparison at the peak surfaces of the internal standards of known IPPd and VPPd concentrations then makes it possible to calculate, by simple linear regression, the initial VPP and IPP content of the sample (generally expressed in mg/kg or ppm).

| Results | |
|---|---|
| | VPPeq. (mg/kg of fermented medium) |
| Calpis CM4 | 51 |
| CNRZ 244 | 57 |
| I-3504 (with 2% (w/w) glucose) | 80 |

Figure 4:
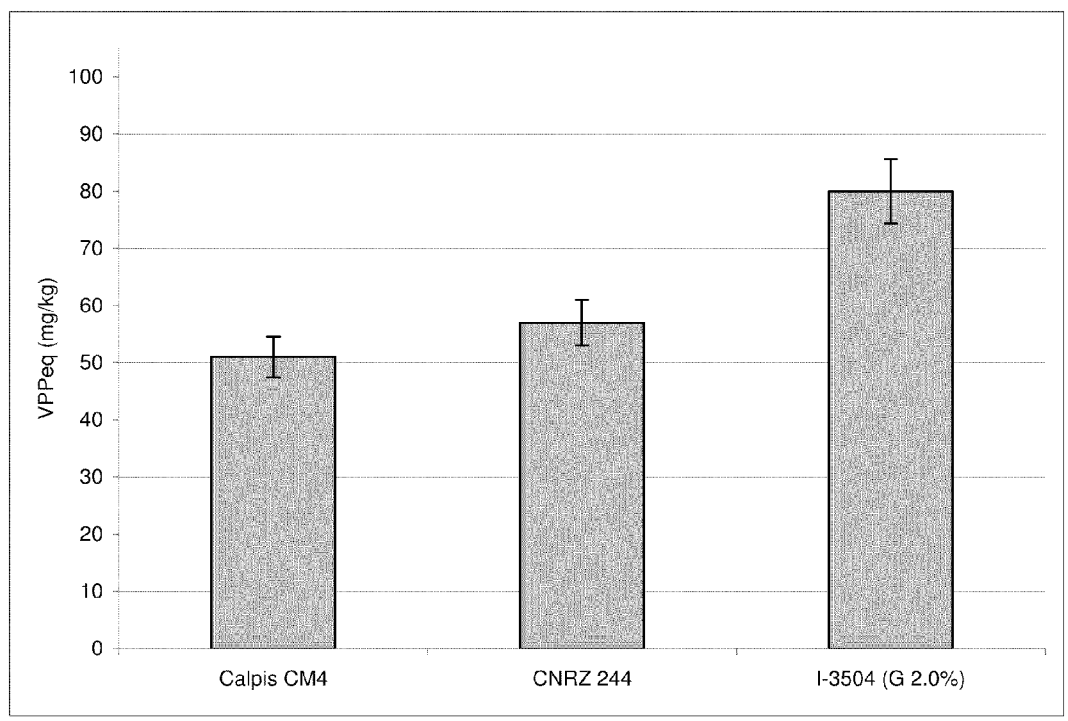

FIG. 4 shows a comparison of the production of tripeptides IPP and VPP of the strain I-3504 (2% (w/w) of glucose are added to the medium) in relation to two strains of the prior art.

The strain CM4 from the company CALPIS is described in the patent EP 1 016 709 whilst the strain CRNZ 244 is described in the Patent Application WO 2004/060073.

It is clear in this figure that the strain I-3504 (strain according to the invention) has a production of tripeptides IPP and VPP much greater than that of these two preceding strains under the same conditions.

Figure 5:
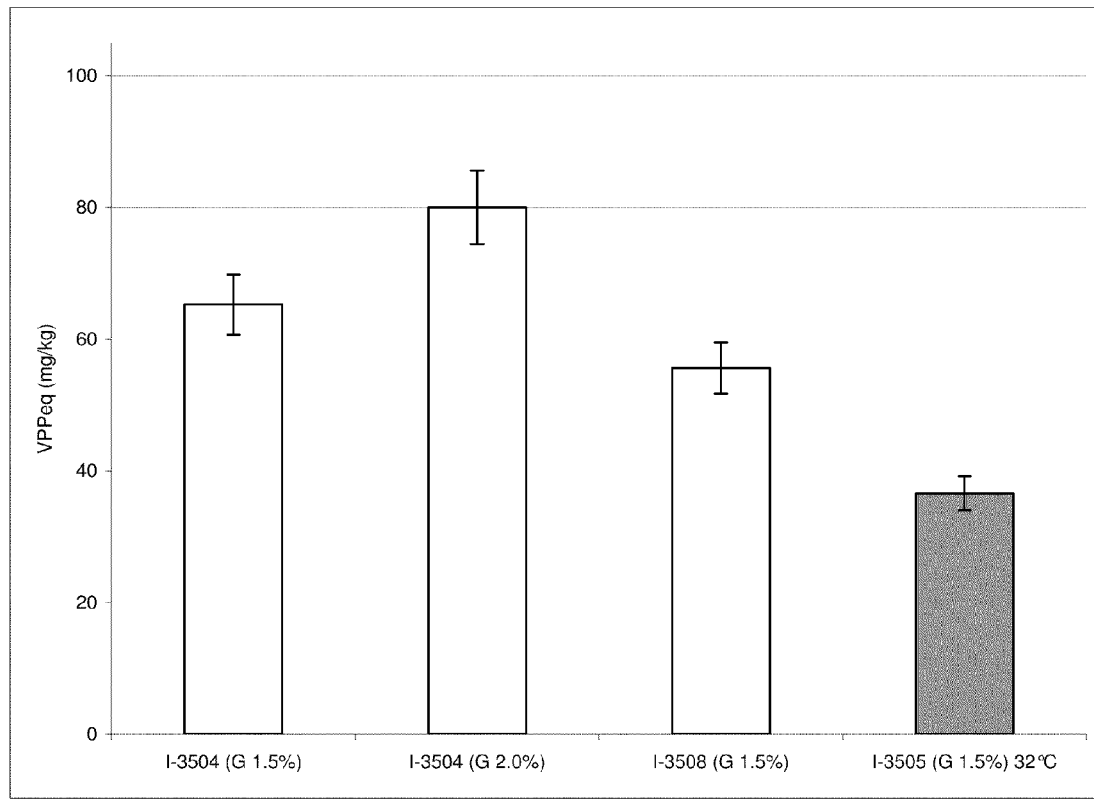

FIG. 5 shows a comparison of the production of tripeptides IPP and VPP of the strains according to the invention with each other.

3. Measurement of the ACEI (Angiotensin Converting Enzyme Inhibition) Activity

Material and Method

A sample of dairy medium taken at 30 hours of fermentation, as described previously under point 1 is used in order to carry out this measurement. The present method is based on the method of Cushman and Cheng (Cushman et al. Biochem. Pharmacol. 1971. 20: 1637), adapted to make it compatible with samples of fermented dairy product type.

1. Preparation of the Reagents and Solutions 1.1 Sodium Borate Buffer 0.1M pH 8.3, Supplemented with 0.3M of NaCl Weigh 6.1843 g of $H_3BO_3$ (Carlo Erba ref: 402 766). Dissolve in approximately 800 ml of demineralized water, adjust to pH 8.3 with a solution of NaOH then add 12.0 g of NaCl (final concentration 0.3 M) and top up to 1 liter with demineralized water.

1.2 Preparation of the HHL Substrate: Solution of Hip-His-Leu at 5 mM in Sodium Borate Buffer 0.1M pH 8.3 with 0.3M of NaCl Weigh exactly 42.95 mg of anhydrous HHL peptide (N-Hippuryl-Histidyl-Leucine tetrahydrate, mol. wt.: 501.5 g, Sigma-Aldrich ref: 53285-250 mg) and dissolve in approximately 15 mL of sodium borate buffer 0.1 M pH 8.3 with 0.3M of NaCl then top up to 20 mL with this same buffer.

1.3 Preparation of the ACE Solution at 0.1 U/mL

The angiotensin converting enzyme in the form of lyophilized powder (origin: rabbit lungs, Sigma-Aldrich ref A6778, 0.25 units) is solubilized in 2.5 mL of sodium borate buffer 0.1M pH 8.3 in order to obtain a solution at 0.1 U/mL. The solution thus prepared must be used, stored at 4° C., after no more than 2 weeks in order to preserve sufficient enzymatic activity.

2. Preparation of the Samples of Fermented Milk

It is necessary to condition the sample at a pH comprised between 8.0 and 8.5 in order to be close to the optimum pH of the ACE. The fermented milk is firstly centrifuged, the pH of the supernatant is then adjusted between 8.0 and 8.5 (ideally pH 8.3) then ultrafiltered using a Vivaspin filtration unit with a cut-off threshold of 10,000 Daltons (Vivascience, France) in order to eliminate the interfering elements (whole proteins, calcium salts).

The complete protocol is as follows:

Place approximately 6 mL of fermented milk in a 15 mL Falcon tube, after having previously weighed the empty tube. Weigh the quantity of fermented milk placed in the tube.

Centrifuge at 14,000 g for 10 minutes at 10° C.

Recover the supernatant

Quantify the proportion of pellet/supernatant which makes it possible if necessary to determine the IC50 equivalent to the original product and not to its supernatant alone.

Place a 2.0 mL sample of supernatant in a test tube and measure the pH.

Add the necessary volume of NaOH 2M in order to obtain a pH comprised between 8.0 and 8.5 (target: 8.3) after addition of the borate buffer, then stir Add the necessary volume of borate buffer in order to dilute the starting supernatant to ½ taking account of the exact volume of NaOH added (for example: test sample of supernatant=2 mL+250 µL NaOH+1.75 mL borate buffer)

Verify that the final pH is comprised between 8.0 and 8.5. Beyond that, start again, adding more or less NaOH. A precipitate forms: this is due to the calcium salts.

Ultracentrifuge the sample at 12,000 g for 15 minutes at 10° C. using 10,000 Dalton Vivaspin filtration units (capacity 4-6 mL) in order to obtain a clear sample.

3. Measurement of ACE Inhibition by the Samples of Fermented Milks

For each analysis series, controls (0 and 100% ACE activity) must be prepared. For each sample, two independent tests and a blank sample are produced for each dilution. It is in fact necessary to adjust as closely as possible (by diluting) the quantity of sample necessary to reduce the activity of the ACE by 50%.

For this purpose:

Place 80 µL of the sample conditioned at pH 8.3 in the blank tube and in the test tubes Place 80 µL of demineralized water in the 0 and 100% control tubes Add 200 µl of the solution of 5 mM HHL substrate to all the tubes. Stir.

Place the tubes in a water bath thermostatically-controlled at 37° C., leave to reach temperature equilibrium Start the enzymatic reaction by the addition of 20 µL of the ACE solution at 0.1 U/mL to each tube, except for the blank samples and 0% control for which 20 µL of borate buffer pH 8.3 must be introduced.

Leave to hydrolyze for exactly 1 hour at 37° C.

Stop the reaction by adding 250 µL of the solution of HCl 1M to each tube.

Summary table of the composition of the different reaction media:

| | Test portion | Addition of substrate | Starting hydrolysis |
|---|---|---|---|
| 100% control | 80 µL of demineralized water | 200 µL of HHL | 20 µL of ACE |
| 0% control | 80 µL of demineralized water | 200 µL of HHL | 20 µL of borate buffer |
| (Test) sample | 80 µL of sample | 200 µL of HHL | 20 µL of ACE |
| Blank sample | 80 µL of sample | 200 µL of HHL | 20 µL of borate buffer |

The reading is taken by extraction of the hydrolyzed substrate (hippuric acid) and its quantification using a spectrophotometer, with the following protocol:

Add 1.7 mL of ethyl acetate to each tube, stir.

Centrifuge at 2000 g for 5 minutes at 10° C.

Place exactly 1 mL of the supernatant in an Eppendorf microtube.

Evaporate the ethyl acetate at 120° C. for 10 minutes in a heating block

Add exactly 1 mL of demineralized water then stir for 10 seconds in order to take up the hippuric acid.

Read the absorbance at 228 nm in cells suitable for UV reading.

Expression of the Results:

The percentage of ACE inhibition is calculated as follows:

$$\frac{(Abs\ 100\%\ ctl - Abs\ 0\%\ ctl) - (Abs\ sam. - Abs\ blank\ sam.)}{(Abs\ 100\%\ ctl - Abs\ 0\%\ ctl)} \times 100$$

With Abs=absorbance at 228 nm after extraction of the hippuric acid ctl=control sam.=sample For a fermented milk, the IC50 is expressed as being the quantity of supernatant of this fermented milk which inhibits 50% of the enzymatic activity of the ACE in the reaction medium, i.e. in microliters of supernatant of fermented milk per milliliter of reaction medium.

Results

Figure 6:
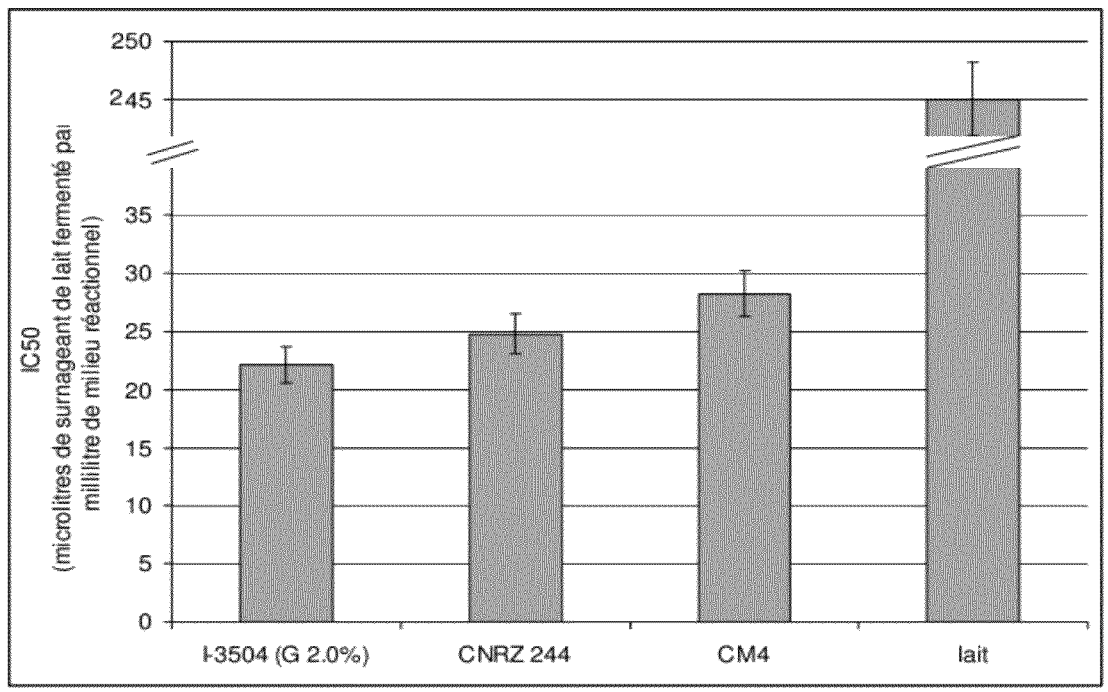

FIG. 6 shows a comparison of the inhibitory activity on the angiotensin converting enzyme of the different strains according to the present invention compared with other strains of the prior art.

The equivalent concentration of fermented milk per ml of reaction medium necessary to inhibit 50% of the activity of the angiotensin converting enzyme (IC50) is expressed along the y-axis. The higher this concentration, the lower the strain's ability therefore to inhibit the angiotensin converting enzyme.

Example 3

Preparation of a (Probiotic) Dairy Product According to the Invention

A fermented dairy product is obtained as indicated below. Bulked milk, previously skimmed, pre-pasteurized and cooled down to 4° C. is standardized as regards proteins (4.0%) with skimmed milk powder and glucose is added to it amounting to 1.8% (w/w). The dairy medium thus prepared is subjected to pasteurization (95° C.—8 minutes). After cooling down to 37° C. the dairy medium is seeded with a strain according to the present invention amounting to $10^7$ CFU/mL and maintained at 37° C. throughout the fermentation period. When pH 3.8 is reached, the curd is removed from the fermentation tank in order to undergo a smoothing process (by passing through a filter) and cooled down to 10° C. in a plate heat exchanger. The smoothed and cooled curd then has a preparation of fruits (having a pH between 4 and 4.1) added to it amounting to 15% of the finished product, packaged in 110 mL bottles and stored at 4° C. for 28 days.

The product thus prepared contains tripeptides of sequence IPP/VPP amounting to 65 mg/kg of VPP equivalent. The peptides content of the product is advantageously stable throughout the life of the product. The reduction in pH during refrigerated storage is advantageously negligible (less than 0.1 unit) and the population of the strains according to the present invention, remains advantageously comprised between $10^7$ and $10^8$ CFU/mL.

Example 4

Identification of Nonsense Point Mutations in the Lactose Operon of Strains According to the Invention Starting with the sequences of the lactose operons of the strains DPC4571 and ATCC15009 available from GenBank, oligonucleotides (primers) were chosen from genes which appeared to be the best preserved. These oligonucleotides made it possible to produce a "long range" PCR, then to begin the sequencing of the lactose operon of strains according to the invention. The sequencing was then carried out stepwise, i.e. depending on the sequences obtained, other primers served for new sequence reactions.

A nonsense mutation was identified in the strain I-3504 in relation to the mother strain I-3431: in the 5'-3' direction, a Cytosine base is replaced by a Thymine, which causes a stop codon to appear at 1320 base pairs of the initiation codon of the lacL gene (which makes approximately 1900 bps) encoding for β-galactosidase.

Apart from this mutation, the lactose operons of the two strains I-3431 and I-3504 are identical.

```
Sequence of the lactose operon of the strain
I-3431 (framed mutation)
                                           (SEQ ID NO: 1)
aaatgaaaattcatgatctaactctggattaatgtgataagcgctttcaa catcagtgccccagctgtcaattcctccaacgccgcgaactgcacctgca attactaacacggttctgcgaacaagtggtagttcttcaatgttagtagc gttctcaagctcctcagcagtataaggcaaacaactgaaattaaatggtt tttctgcttgttgaattgagagactgaacttttcatttgtacgatctaca ttattttgtgtggtttcacgattaatggttaacttcttagtttgcatgtg cattccattttcctgcggaaccaaatactcggtaactggcaaaccatcga tatggaatttaccttctttagctccagccattctatcaggataagtttca ccggataaaccttcataatcaaatcctgtagcagccgttggcataatcaa tcgaataccaattacaggcaggggtggtaatcccttcttaccataataac gcattgtaaccttaatgtgaccgacatcatcaatattatagatgattttt gcatttgttgcaggagtagttaaagtttgataggtaaatgaaatttcagc acttttttgcatactcgtgattgctaaatttgttgttaaagggtgcaatag gcagttcggcaaagtcatgtctgtctacttttaaatggatatcagtacat ttagtaaacatatcagctccgagccattgagctgcctttagattaaatcc actgcctcggtcgttatctgtagttgctcgcaaaaagtaggagtaggta cacgataaagccattccttgccgtgtacttttaacgattcaagtccgccg cgttcataactaaagatgtattgaaaatctttgccattaacgccaaatgt ggcatcccataaatgatatgcaattgattatttgtgtaatccataatag tatctcacttcctgcatagctggtttggttttctatctgcgaacattaa accatcgccagaaaattcataatctgaatgacgatcatcaaaattgccgc cataacgcaaaacatcatgtccactaatttcatcatgaaccaataatgcc tgatcgataaagtcccagataaatccaccgaagtattgagggtatttatc aagtaatttgatatatgaatccatgccgccgttagaattgcccatgtcat gcatatattcgcattccataaatggctttggtggatcattttgcaagtat tcttcaacctttttaggtggtaaatacatacagctttcaacatctgaaat tttatctttaattcgggacggtgcactacgccttcatagtgaactaagc gtgtatcatcgtgagatttgtaaaattcattcattgcgatgatgttgtct ccagcataggattcgttgccaagtgaccaaaagagaatagaggtgtgatt cttgaaagtctcgtagttattgcgtgctcgatcaatcactgcttctttc attgcggaatcgaacctggtacattgtcagaaggttcaatctctcccatt ttttgccaagtaccatgtgattcaaggttattctcggccatgacataaat gccatttgatcgcaaagataataccacggaatttggtttgggtagtgac atgttctaacagcattaatattattttctttaaaagtattaatgtcagtt gtcatatcactcattgttatgctgcgaccacgttttgcatcccattcatg tcggttaactccattgataattaaacgcttgccatttaacaaaacaactt tttctggactaatttcaattctcctaaagccaaattggaaaggaatcagc tctagcaagttttgttgttcatcataaacttcaattagaagctgataaag atatggatcatggttattccaaagatgcacgttttcgaatttttcattat taatttgaacgttctctttgatatcttcatttttctccagaagagtatgt cccttaatatctttgactaataaatggaatgaaccggatttttttaccaat aaaatgaagcttaaggttgaagatgccatcttgataattatctgcaactc gtggtttcaaatccatgtccattaagtgggtagcgggatacctagtagt tcaactgagcggaagatgccagagaagcggaacatgtcttggtcttctag ccaagatgcagtactgtgtttaaaaacttctactgctaaaagattatctt tttcttgaatatatggcgttaaatcaaattctgaaggagtaaagctgtct tccgcatagcccacaaaatgcccgtttaaccatacatacattgcttttttc gacgccttcaaatttaatatgaacatcttttccaattaaggctgagctta aatcaaatcgcttcaagtatgaaccgactgtgttatctgcgcctttgcta aatgagccttcttcatgatcattaggatctaaagcgtaagctgggcggcg gaagattttgccttcccaaggaaggaggacattaatatattgattttgag tatagttgctcaattcgatttcacttggaactgggatcgaatcaaaattt gaagaatcaaaatcacgctgataaaaatcttgtggacgatccataggatt agcggaaaaatgaaatttccattttccattttaaactttgttgatagctac tgtgttgcttttgccactcgcgataatctctaaaaaagggatgatcactg tgtgcgggcaattgattgaccctgaataacctcaggattatctagccaatt gatatttgcttgcataatatgacctcatttctattaaaatatatttcgaa agcgcttttattatagcatgtaaataaacaatttattagtattagtaaag aattttatttacaatatttaataagatttacttgctataaagactgaatac atgcagataatagaacctttatttattggaatttagtaaatattttgtat aataaagaaagagaatttataaaaatagaaaagaaataattatgagaaca attaaagaaattgcgctggaatcaggctattctccagcgacagtatcacg tttattaaataatgatcctaatttgtctattactgcagataccaaaaata agatttggagattgctaataaattgggctattgggaagatcatcaagaa aagaaaatcaagcccacaattgctttactttatcgagtaaatcataagga acaattgcaggatgagtatttcacttcgttgaaacaagcattagtttcaa ctgtagagcgagatgcgctgaagatgaaaaacttttatgacatagaagat ttaatcaagaacgcttcttttgttccaaggatttattggagtaggggcga gccaattgaaaacgcccagttggttaagctgcataaagttttgcctaatg
```

-continued

```
gtgtttttgttgataccaatccagctcccgaattatttgattcaattcgc
cctaatctgcctcttacggttaaaaatgctattgatttgtttatcaaaaa
tggcattaacaagatcggttttatcggtggcgttggccctaagcatgacc
atattcaggaaaaagatttgcgttcaattacttttgttgaatacatgaaa
actagaggcatggatactaaatggacatgcgttgaaggaccggttagcgt
tgaaaatggttataaattgggaaaaatggttttggctaaatacaaaaatg
atttacctgaagcattttttaattgcatctgatactttagccgttggcgtt
ttacaagccttttaacgaagaaaacgtaaatgtaccaaaagatactaagat
cttaagtattaataatagcaatgtggttaagtatgtttcaccaccacttt
cttcgttcaacattaatcaacaagaaatgattgatatggcacttgatact
ttgactcatttgattattcatccagatcgaccaaagattgatatccggat
gaacactaatttggtagtacgaaaaagcttcgttccccaagaaaagtaaa
ttttttagtaaaaaaatattttttgatagaaaataaaaaagagaatgtga
acagctcacattctctttttatttacttagttaacaaaggagcgtatatg
actttcatgcaaacgattgcagagattcattggggaggaaggaaaaagat
gaataatcataaaatctcaggaaagcaagtcatttcctatgcgtcctttt
gtttggggaatttaggatacgcagcttttatggcgtaatgagtacgtat
tttattattttttatcactagtgccatgtttacaggactagatcattcagt
tgcagataagttaattggcttaattactgcattgatagttttagtaagaa
attgtagagttagtaattgatccagtgttggggaacatcgttgataatac
taaaacaaggtgaggcaagtttaagccttggatctttattggaacggtag
ctagtgccgcattactgctaattctctttactggtattttcggcttggca
cataagagttggattctttttgcaatttttatttgtaatcatttatatcgg
ttttgacgttttttattccttatcagatggggcatggttccagccttaag
tgaggattcacacgcacgtggtatttatactgctttggggacttttttcag
gtgcaattggttggaacggactaactatcattgttgtgccactggttacc
ggtgtaacttatgcaatgactggcaagcatgaagaaggggctcctggttg
gtttgcctttgcggcggttatttcagccttagctattctttgtgcactaa
tcgtatgtttaggaactaatgaaaaacataatttaattagaaattctgcc
aagtaaaaaacaactttaggtcaagtatttggggcaatttcacataatga
tcagattttatagccaagtttggcttatttgatgttctcattggctaatg
taattacaaatggggtaatgtttttatctgtacaaattcgtgattaataaa
ccaaatgacttctgggttgttggtgtcattgccacattaatcgttttttg
cattagtccattgtttccaattttaaataaatatattccaagaaaatggc
tatttattggcggtcaaatttgtatgattttggcatacgggttgttcatt
ttcggtcgcaataacgtcatttttaatggatttaggggttagctctatttaa
tatcaactttgctcaattagtaactgttttaacattaactgatgccatcg
aatatggtcagctgaaaagtggtcagagaaatgaagccgtcgttttagct
gttcgaccaatggtcgataaatttaccggtgctatttcaaacgcgctagt
aggatatgtagcaattgcggcaggcatgactggttcagcaactgcagcag
atagacaagtcacgatattagcattttcaatattatggctttatatgtgc
```

-continued

```
cattaattttggcagttttagctattatcattttttataagcaaggtaact
ttatctgaaaagaaacacgctcaagtggttgaagaattaaagagcaaact
tgcacaagggaagatcgaagatggcaatttacctgcagcaaatttaaagt
cgactgccatttatgcacctgcagatggtaaattaatgactatgtctgaa
gtaatcgatgaaaatggcaaaacatttcctggtaaaggctttgcaatcga
tccaagcagtgggcaaattttttgccacatttgatggtaaaattaagttta
cctttggtaccaagcatgcgtttgaaattgtaactgaaaatggtctgcaa
gttatagttcacgttggtcttggcacagttaatttgcgtggtgaaggatt
tgagtcatattatgatgatggacaaattgttaaaaaaggtgaactgctat
tagaatctgaccgtgatttagcactaaaaaatggttataaagatacgata
gtaattttctatactcaacctggtagagtagaaaaaaatgagtaaaatttc
ggcaggtaaagttgttgaacatggtcaaaaggtggttgaagtgaagttta
agtagaggaaactgatgtaagcataaatttaatattgatttacatgtata
aaaaagaatgacttttagtgttaagtaaacttttttggtaaagaaaaaatt
ttataagccttttttttaaaaaaagaatgacgtaaataagccttttcttt
aaatatttatacttagtaaatagcttagtaaatctaaataaatattttac
tagaacaaaaaaaatgataaattatttcgtgtaagcgatttctgaaaag
gaatcttgggaggaattatcatgcataatcataaagtttcggggaaacaa
atagtttcctatgcatcattttgtctgggcaatttggggcactcagcatt
ttatggtgtaatgagtacatattttattattttttattactagtggaatgt
ttagcggattaaatcaatccgttgctgataaaattagtaggtttaattact
ggattaatggtactagtaagaattatcgaactagtcattgaccctatttt
tgcagcattattacttattctatttactggtattttggattagcacaac
agaattggatccttttgcaatttttgtttgtgttgatttacatcgcttt
gatgtttctattcattatcagatgtttcatattggggcatggttccagc
tttgagtgaagattcacatgaacgtggtatttatacttcacttggtgcct
tttcaggtactattggttggaatagtttgccaattattgttgtgccactg
gttaccggtgtaacttacgcggttactggcaaacacgaagaaggagctcc
tggctggttcgcctttgcggccgtaatttcagccttagcaattatttgtg
ccttgattgtttgctttggtactaaagaaaagcacaacattattagaaat
tcggccaaacagaaaaccactttgcgtcaagtatttggtgcgattttcca
taatgatcaaattttgtggccaagtttagcttacttattgtattcacttg
ctgttgtaattactaatggtgttttgttctacatgtacaagtttgtaatt
ggcaagccaaatgatttctgggtagtaggtgtaattgcaacaattattgg
ttgctgcattagtccatctttcccggttttgaacaaatatattccaagaa
aatggttgtttattgcaggccaaacttgtatggtattagcatatgtccta
tttatctttggtcgtaacaatgtcttcttaatggatttaggcttagtttt
attcaatattaacttcgctctgttggtaactgttttaactttaactgatg
ctattgaatatggtcaacttaagattggtcaaagaaatgaagccgttgtt
ttagctgttcgtccaatgattgataaattactggtgctgtttcaaatgc
```

-continued

```
cttagttggttatgtggcaattgcagctgggatgactggatcagctactg cagcagatatgacgagcaaaggtattaacacatttaatattatggcttta tatattcctttagctttggcagttttatctattgtagtattttgagcaa agtaactttgagtgaaaagaaacacgcacaagttattgaagaattgaaga gtaaacttgcacaaggcgagattgaaaagaagacttcagtagatacagga acaaaagaagtaactatttatgcacctgctgatggtgaattaatgcaaat gtcttctgttgttgatgaagatggtaaaccattccctggtaaaggatttg caattgagccaagcagtggtcaaatttatgcaccatttgatggaacgatc aagtttactttcggtacaaagcatgcattcgagattgtgtcacaaaatgg actacaagttgttgtccatgtaggattgggtactgtcaatttacgtggag aaggctttgaaactttctacgatgatggtcaaacagtgaaaagggcgat
```

-continued

```
aaattacttgagtttgatcgtgatttggctcttaacaatggttataaaga cacgatcgtgatattctatactcaaccaggtagaattcaaaattctggtg ctattcaagctggtaaagatat
```

Similarly, analyses of sequencings reveal the following mutations in the lactose operon of strains according to the invention:

Strain I-3505 by Comparison with Strain I-3434:

In strain I-3505, an adenosine base replaces a guanine base which causes the appearance of a stop codon, at 1713 base pairs from the start of the lacL gene encoding for betagalactosidase.

Strain I-3508 by Comparison with Strain I-3435:

In strain I-3508, an adenosine base replaces a guanine base which causes the appearance of a stop codon, at 183 base pairs from the start of the lacL gene encoding for betagalactosidase.

The invention claimed is:

1. A biologically pure culture of *Lactobacillus helveticus* obtained from a strain having an accession number I-3431, I-3434, or I-3435 as deposited with Collection Nationale de Culture de Microorganismes (CNCM) that is incapable of converting lactose into lactic acid, wherein said strain is capable of producing the tripeptides of sequence IPP and/or VPP in a quantity of at least 25 mg of VPP equivalent (VPPeq) per kg of fermented product,
wherein said tripeptides are produced by fermentation at a temperature between 30 and 45° C. of a dairy medium containing a quantity of glucose greater than 3% (w/w) and with a total proteins content greater than or equal to 2% (w/w).

2. The culture according to claim 1, having at least one mutation in the lactose operon.

3. The culture according to claim 2, having at least one point mutation introducing a stop codon in the lactose operon.

4. The culture according to claim 1, which further has a fructose-negative phenotype.

5. The culture of *Lactobacillus helveticus* according to claim 1, wherein the strain is selected from the group consisting of:
*Lactobacillus helveticus* having an accession number I-3504 as deposited with CNCM;
*Lactobacillus helveticus* having an accession number I-3505 as deposited with CNCM; and
*Lactobacillus helveticus* having an accession number I-3508 as deposited with CNCM.

6. A food product comprising at least $10^6$ CFU/mL of live *Lactobacillus helveticus* bacteria from a culture of *Lactobacillus helveticus* according to claim 1.

7. The food product according to claim 6, further comprising at least 25 mg of VPPeq per kg of said food product.

8. The food product according to claim 6, further comprising fruit pieces and/or fruit juices.

9. The food product according to claim 6, possessing a pH greater than or equal to 3.85.

10. The food product according to claim 6, having antihypertensive properties in humans.

11. The food product according to claim 6, wherein the food product is a dairy product selected from the group consisting of milk, cream, ice cream, butter, cheese, yogurt, fermented milk, cottage cheese and kefir.

12. The food product according to claim 6, wherein the food product is a fermented dairy product.

13. The culture according to claim 1, wherein the temperature is between 32° C. and 43° C.

14. The culture according to claim 1, wherein the temperature is 37° C.

15. The culture according to claim 1, wherein the total protein content is between 2% and 10% (w/w).

16. The culture according to claim 1, wherein the total protein content is between 2.5% and 6%.

17. The culture according to claim 1, wherein the total protein content is 4%.

18. The culture according to claim 1, wherein the culture is capable of producing the tripeptides of sequence IPP and/or VPP in a quantity of 50 mg of VPPeq per kg of said fermented product.

19. The culture according to claim 1, wherein the culture is capable of producing the tripeptides of sequence IPP and/or VPP in a quantity of at least 75 mg of VPPeq per kg of said fermented product.

20. The food product according to claim 6, further comprising tripeptides of sequence IPP and/or VPP in quantities of at least 50 mg of VPPeq per kg of said food product.

21. The food product according to claim 20, wherein the quantity of the tripeptides of sequence IPP and/or VPP is at least 75 mg of VPPeq per kg of said food product.

22. The food product according to claim 6, comprising at least $10^7$ CFU/mL of the live *Lactobacillus helveticus* bacteria.

23. The food product according to claim 6, comprising at least $10^8$ CFU/mL of the live *Lactobacillus helveticus* bacteria.

* * * * *

UNITED STATES PATENT AND TRADEMARK OFFICE
CERTIFICATE OF CORRECTION

PATENT NO. : 8,323,951 B2  
APPLICATION NO. : 12/279951  
DATED : December 4, 2012  
INVENTOR(S) : Garault et al.

Page 1 of 1

It is certified that error appears in the above-identified patent and that said Letters Patent is hereby corrected as shown below:

On the title page, item (75), under "Inventors", in Column 1, Line 3, delete "Jean-Michael Faurie," and insert -- Jean-Michel Faurie, --, therefor.

In the Claims

Column 25, Line 11, in Claim 1, delete "between 30 and 45 C." and insert -- between 30 °C and 45 °C --, therefor.

Column 25, Line 22, in Claim 5, delete "helveticusaccording" and insert -- helveticus according --, therefor.

Signed and Sealed this  
Fourth Day of November, 2014

Michelle K. Lee  
*Deputy Director of the United States Patent and Trademark Office*

SEQUENCE LISTING

<160> NUMBER OF SEQ ID NOS: 1

<210> SEQ ID NO 1
<211> LENGTH: 8172
<212> TYPE: DNA
<213> ORGANISM: Lactobacillus helveticus
<220> FEATURE:
<221> NAME/KEY: misc_feature
<222> LOCATION: (1)..(8172)
<223> OTHER INFORMATION: Strain I-3431

<400> SEQUENCE: 1

```
aaatgaaaat tcatgatcta actctggatt aatgtgataa gcgctttcaa catcagtgcc      60
ccagctgtca attcctccaa cgccgcgaac tgcacctgca attactaaca cggttctgcg     120
aacaagtggt agttcttcaa tgttagtagc gttctcaagc tcctcagcag tataaggcaa     180
acaactgaaa ttaaatggtt tttctgcttg ttgaattgag agactgaact tttcatttgt     240
acgatctaca ttattttgtg tggtttcacg attaatggtt aacttcttag tttgcatgtg     300
cattccattt tcctgcggaa ccaaatactc ggtaactggc aaaccatcga tatggaattt     360
accttcttta gctccagcca ttctatcagg ataagtttca ccggataaac cttcataatc     420
aaatcctgta gcagccgttg gcataatcaa tcgaatacca attacaggca ggggtggtaa     480
tcccttctta ccataataac gcattgtaac cttaatgtga ccgacatcat caatattata     540 gatgatttt gcatttgttg caggagtagt taaagtttga taggtaaatg aaatttcagc     600 acttttgca tactcgtgat tgctaaattt gttgttaaag ggtgcaatag gcagttcggc     660
aaagtcatgt ctgtctactt ttaaatggat atcagtacat ttagtaaaca tatcagctcc     720
gagccattga gctgccttta gattaaatcc actgcctcgg tcgttatctg tagttgctcg     780
ccaaaaagta ggagtaggta cacgataaag ccattccttg ccgtgtactt ttaacgattc     840
aagtccgccg cgttcataac taaagatgta ttgaaaatct ttgccattaa cgccaaatgt     900
ggcatcccca taaatgatat gcaattgatt atttgtgtaa tccataatag tatctcactt     960
cctgcatagc tggttttggt tttctatctg cgaacattaa accatcgcca gaaaattcat    1020
aatctgaatg acgatcatca aaattgccgc cataacgcaa aacatcatgt ccactaattt    1080
catcatgaac caataatgcc tgatcgataa agtcccagat aaatccaccg aagtattgag    1140
ggtatttatc aagtaatttg atatatgaat ccatgccgcc gttagaattg cccatgtcat    1200
```

```
gcatatattc gcattccata aatggctttg gtggatcatt ttgcaagtat tcttcaacct   1260 tttaggtgg taaatacata cagctttcaa catctgaaat tttatctttt aattcgggac   1320
ggtgcactac gccttcatag tgaactaagc gtgtatcatc gtgagatttg taaaattcat   1380
tcattgcgat gatgttgtct ccagcatagg attcgttgcc aagtgaccaa aagagaatag   1440
aggtgtgatt cttgaaagtc tcgtagttat tgcgtgctcg atcaatcact gcttcttttcc  1500 attgcggaat cgaacctggt acattgtcag aaggttcaat ctctcccatt ttttgccaag   1560
taccatgtga ttcaaggtta ttctcggcca tgacataaat gccatttga tcgcaaagat    1620 aataccacgg aatttggttt gggtagtgac atgttctaac agcattaata ttattttctt   1680
taaaagtatt aatgtcagtt gtcatatcac tcattgttat gctgcgacca cgttttgcat  1740
cccattcatg tcggttaact ccattgataa ttaaacgctt gccatttaac aaaacaactt   1800
tttctggact aatttcaatt ctcctaaagc caaattggaa aggaatcagc tctagcaagt   1860
tttgttgttc atcataaact tcaattagaa gctgataaag atatggatca tggttattcc   1920
aaagatgcac gttttcgaat ttttcattat taatttgaac gttctctttg atatcttcat   1980
ttttctccag aagagtatgt cccttaatat cttttgactaa taaatggaat gaaccggatt  2040
ttttaccaat aaaatgaagc ttaaggttga agatgccatc ttgataatta tctgcaactc   2100
gtggtttcaa atccatgtcc attaagtggg tagcggggat acctagtagt tcaactgagc   2160
ggaagatgcc agagaagcgg aacatgtctt ggtcttctag ccaagatgca gtactgtgtt   2220 taaaacttc tactgctaaa agattatctt tttcttgaat atatggcgtt aaatcaaatt    2280
ctgaaggagt aaagctgtct tccgcatagc ccacaaaatg cccgtttaac catacataca   2340 ttgcttttc gacgccttca aatttaatat gaacatcttt tccaattaag ctgagctta    2400 aatcaaatcg cttcaagtat gaaccgactg tgttatctgc gcctttgcta atgagccctt   2460
cttcatgatc attaggatct aaagcgtaag ctgggcggcg gaagattttg ccttcccaag   2520
gaaggaggac attaatatat tgattttgag tatagttgct caattcgatt tcacttggaa   2580
ctgggatcga atcaaaattt gaagaatcaa aatcacgctg ataaaaatct tgtgacgat    2640 ccataggatt agcggaaaaa tgaaatttcc attttccatt taaactttgt tgatagctac   2700
tgtgttgctt ttgccactcg cgataatctc taaaaaaggg atgatcactg tgtgcgggca   2760
attgattgac cctgaatacc tcaggattat ctagccaatt gatatttgct tgcataatat   2820
gacctcattt ctattaaaat atatttcgaa agcgcttttta ttatagcatg taaataaaca  2880
atttattagt attagtaaag aatttatta caatatttaa taagatttac ttgctataaa    2940
gactgaatac atgcagataa tagaaccttt atttattgga atttagtaaa tattttgtat   3000
aataaagaaa gagaatttat aaaaatagaa aagaaataat tatgagaaca attaaagaaa   3060
ttgcgctgga atcaggctat tctccagcga cagtatcacg tttattaaat aatgatccta   3120
atttgtctat tactgcagat accaaaaata agattttgga gattgctaat aaaattgggct 3180 attgggaaga tcatcaagaa aagaaaatca agcccacaat tgctttactt tatcgagtaa   3240
atcataagga acaattgcag gatgagtatt tcacttcgtt gaaacaagca ttagtttcaa   3300
ctgtagagcg agatgcgctg aagatgaaaa actttttatga catagaagat ttaatcaaga  3360
acgcttcttt gttccaagga tttattggag taggggcgga gccaattgaa aacgcccagt   3420
tggttaagct gcataaagtt ttgcctaatg gtgttttttgt tgataccaat ccagctcccg  3480
aattatttga ttcaattcgc cctaatctgc ctcttacggt taaaaatgct attgatttgt   3540
ttatcaaaaa tggcattaac aagatcggtt ttatcggtgg cgttggccct aagcatgacc   3600
```

```
atattcagga aaaagatttg cgttcaatta cttttgttga atacatgaaa actagaggca    3660
tggatactaa atggacatgc gttgaaggac cggttagcgt tgaaaatggt tataaattgg    3720
gaaaaatggt tttggctaaa tacaaaaatg atttacctga agcatttttta attgcatctg   3780 atactttagc cgttggcgtt ttacaagcct ttaacgaaga aaacgtaaat gtaccaaaag    3840
atactaagat cttaagtatt aataatagca atgtggttaa gtatgtttca ccaccacttt    3900
cttcgttcaa cattaatcaa caagaaatga ttgatatggc acttgatact ttgactcatt    3960
tgattattca tccagatcga ccaaagattg atatccggat gaacactaat ttggtagtac    4020
gaaaaagctt cgttccccaa gaaagtaaaa tttttttagta aaaaaatatt ttttgataga   4080
aaataaaaaa gagaatgtga acagctcaca ttctctttttt atttacttag ttaacaaagg   4140
agcgtatatg actttcatgc aaacgattgc agagattcat tggggaggaa ggaaaaagat    4200
gaataatcat aaaatctcag gaaagcaagt catttcctat gcgtcctttt gtttggggaa    4260
tttaggatac gcagcttttt atggcgtaat gagtacgtat tttattattt ttatcactag    4320
tgccatgttt acaggactag atcattcagt tgcagataag ttaattggct taattactgc    4380
attgatagtt ttagtaagaa attgtagagt tagtaattga tccagtgttg gggaacatcg    4440
ttgataatac taaaacaagg tgaggcaagt ttaagccttg gatctttatt ggaacggtag    4500
ctagtgccgc attactgcta attctctttta ctggtatttt cggcttggca cataagagtt   4560
ggattctttt tgcaatttta tttgtaatca tttatatcgg ttttgacgtt ttttattcct    4620
tatcagatgg ggcatggttc cagccttaag tgaggattca cacgcacgtg gtatttatac    4680
tgctttgggg actttttcag gtgcaattgg ttggaacgga ctaactatca ttgttgtgcc    4740
actggttacc ggtgtaactt atgcaatgac tggcaagcat gaagaagggg ctcctggttg    4800
gtttgccttt gcggcggtta tttcagccct agctattctt tgtgcactaa tcgtatgttt    4860
aggaactaat gaaaaacata atttaattag aaattctgcc aagtaaaaaa caactttagg    4920
tcaagtattt ggggcaattt cacataatga tcagatttta tagccaagtt tggcttattt    4980
gatgttctca ttggctaatg taattacaaa tggggtaatg ttttatctgt acaaattcgt    5040
gattaataaa ccaaatgact tctgggttgt tggtgtcatt gccacattaa tcgtttttttg   5100 cattagtcca ttgttttccaa ttttaaataa atatattcca agaaaatggc tatttattgg    5160
cggtcaaatt tgtatgattt tggcatacgg gttgttcatt ttcggtcgca ataacgtcat    5220
tttaatggat ttagggttag ctctatttaa tatcaacttt gctcaattag taactgttttt   5280 aacattaact gatgccatcg aatatggtca gctgaaaagt ggtcagagaa atgaagccgt    5340
cgttttagct gttcgaccaa tggtcgataa atttaccggt gctatttcaa acgcgctagt    5400
aggatatgta gcaattgcgg caggcatgac tggttcagca actgcagcag atagacaagt    5460
cacgatatta gcattttcaa tattatggct ttatatgtgc cattaatttt ggcagtttta    5520
gctattatca tttttataag caaggtaact ttatctgaaa agaaacacgc tcaagtggtt    5580
gaagaattaa agagcaaact tgcacaaggg aagatcgaag atggcaattt acctgcagca    5640
aatttaaagt cgactgccat ttatgcacct gcagatggta aattaatgac tatgtctgaa    5700
gtaatcgatg aaaatggcaa aacatttcct ggtaaaggct ttgcaatcga tccaagcagt    5760
gggcaaattt ttgccacatt tgatggtaaa attaagttta cctttggtac caagcatgcg    5820
tttgaaattg taactgaaaa tggtctgcaa gttatagttc acgttggtct tggcacagtt    5880
aatttgcgtg gtgaaggatt tgagtcatat tatgatgatg acaaattgt taaaaaaggt     5940 gaactgctat tagaatctga ccgtgattta gcactaaaaa atggttataa agatacgata    6000
```

```
gtaattttct atactcaacc tggtagagta gaaaaaatga gtaaaatttc ggcaggtaaa    6060
gttgttgaac atggtcaaaa ggtggttgaa gtgaagttta agtagaggaa actgatgtaa    6120
gcataaattt aatattgatt tacatgtata aaaagaatg  actttttagtg ttaagtaaac   6180
tttttggtaa agaaaaaatt ttataagcct ttttttttaaa aaaagaatga cgtaaataag   6240
cctttctttt aaatatttat acttagtaaa tagcttagta aatctaaata aatattttac    6300
tagaacaaaa aaaatgata  aattatttcg tgtaagcgat ttctgaaaag gaatcttggg    6360
aggaattatc atgcataatc ataaagtttc ggggaaacaa atagtttcct atgcatcatt    6420
ttgtctgggc aatttggggc actcagcatt ttatggtgta atgagtacat attttattat    6480
ttttattact agtggaatgt ttagcggatt aaatcaatcc gttgctgata aattagtagg    6540
tttaattact ggattaatgg tactagtaag aattatcgaa ctagtcattg accctatttt    6600
tgcagcatta ttacttattc tatttactgg tatttttgga ttagcacaac agaattggat    6660
ccttttttgca attttgtttg tgttgattta catcgctttt gatgttttct attcattatc    6720
agatgtttca tattggggca tggttccagc tttgagtgaa gattcacatg aacgtggtat    6780
ttatacttca cttggtgcct tttcaggtac tattggttgg aatagtttgc caattattgt    6840
tgtgccactg gttaccggtg taacttacgc ggttactggc aaacacgaag aaggagctcc    6900
tggctggttc gcctttgcgg ccgtaatttc agccttagca attatttgtg ccttgattgt    6960
ttgctttggt actaaagaaa agcacaacat tattagaaat tcggccaaac agaaaaccac    7020
tttgcgtcaa gtatttggtg cgattttcca taatgatcaa attttgtggc caagtttagc    7080
ttacttattg tattcacttg ctgttgtaat tactaatggt gttttgttct acatgtacaa    7140
gtttgtaatt ggcaagccaa atgatttctg ggtagtaggt gtaattgcaa caattattgg    7200
ttgctgcatt agtccatctt tcccggtttt gaacaaatat attccaagaa atggttgtt    7260
tattgcaggc caaacttgta tggtattagc atatgtccta tttatctttg gtcgtaacaa    7320
tgtcttctta atggatttag gcttagtttt attcaatatt aacttcgctc tgttggtaac    7380
tgttttaact ttaactgatg ctattgaata tggtcaactt aagattggtc aaagaaatga    7440
agccgttgtt ttagctgttc gtccaatgat tgataaattt actggtgctg tttcaaatgc    7500
cttagttggt tatgtggcaa ttgcagctgg gatgactgga tcagctactg cagcagatat    7560
gacgagcaaa ggtattaaca catttaatat tatggcttta tatattcctt tagctttggc    7620
agttttatct attgtagtat ttttgagcaa agtaactttg agtgaaaaga aacacgcaca    7680
agttattgaa gaattgaaga gtaaacttgc acaaggcgag attgaaaaga agacttcagt    7740
agatacagga acaaaagaag taactattta tgcacctgct gatggtgaat taatgcaaat    7800
gtcttctgtt gttgatgaag atggtaaacc attccctggt aaaggatttg caattgagcc    7860
aagcagtggt caaatttatg caccatttga tggaacgatc aagtttactt tcggtacaaa    7920
gcatgcattc gagattgtgt cacaaaatgg actacaagtt gttgtccatg taggattggg    7980
tactgtcaat ttacgtggag aaggctttga aactttctac gatgatggtc aaacagtgaa    8040
aaagggcgat aaattacttg agtttgatcg tgatttggct cttaacaatg ttataaaga    8100
cacgatcgtg atattctata ctcaaccagg tagaattcaa aattctggtg ctattcaagc    8160
tggtaaagat at                                                       8172
```